(12) United States Patent
Mink et al.

(10) Patent No.: US 8,772,339 B2
(45) Date of Patent: Jul. 8, 2014

(54) ETHYLGALLATE AND RELATED COMPOUNDS AS A TREATMENT FOR SEPSIS AND SEPTIC SHOCK

(76) Inventors: Steven N. Mink, Winnipeg (CA); Hans Jacobs, Roesrath (DE)

( * ) Notice: Subject to any disclaimer, the term of this patent is extended or adjusted under 35 U.S.C. 154(b) by 365 days.

(21) Appl. No.: 13/387,050

(22) PCT Filed: Feb. 24, 2010

(86) PCT No.: PCT/CA2010/000221
§ 371 (c)(1),
(2), (4) Date: Jun. 14, 2012

(87) PCT Pub. No.: WO2010/096906
PCT Pub. Date: Sep. 2, 2010

(65) Prior Publication Data
US 2012/0277312 A1    Nov. 1, 2012

Related U.S. Application Data

(60) Provisional application No. 61/154,986, filed on Feb. 24, 2009.

(51) Int. Cl.
*A01N 37/10*    (2006.01)
*A61K 31/235*    (2006.01)
*C07C 69/00*    (2006.01)

(52) U.S. Cl.
USPC .......................................... 514/544; 560/129

(58) Field of Classification Search
CPC ...... A61K 31/21; C07D 213/55; C07D 271/22
USPC .......................................... 514/544; 560/129
See application file for complete search history.

(56) References Cited

FOREIGN PATENT DOCUMENTS

EP    1481669 A1 * 12/2004

OTHER PUBLICATIONS

Chang et. al., Infection and Immunology, 2001, American Society for Microbiology, vol. 69, No. 12, pp. 7341-7348.*
Maag, Prodrugs: Rewards and Challenges, 2007, AAPS Press, vol. 5, pp. 5 and 8-11.*

* cited by examiner

*Primary Examiner* — Sarah Pihonak
(74) *Attorney, Agent, or Firm* — Michael R. Williams; Ade & Company Inc.

(57) ABSTRACT

The use of ethyl gallate methyl gallate or 3,4-dihydroxybenzoate for treatment of septic shock Said compounds may also prophylactically treat septic shock via administration to a subject before the development of a fall in blood pressure.

4 Claims, 12 Drawing Sheets

ETHYLGALLATE AND RELATED COMPOUNDS AS A TREATMENT FOR SEPSIS AND SEPTIC SHOCK

PRIOR APPLICATION INFORMATION

The instant application claims the benefit of U.S. Provisional Patent Application 61/154,986, filed Feb. 24, 2009.

BACKGROUND OF THE INVENTION

Lysozyme is a newly discovered mediator of sepsis that has been shown to produce vasodilation and myocardial depression in canine models of septic shock (1-7). Lysozyme produces vasodilation by intrinsically generating hydrogen peroxide ($H_2O_2$) that leads to activation of signaling pathways resulting in these hemodynamic effects (7). In recent in-vitro studies, we showed that the antioxidants, ethyl gallate, methyl gallate, and ethyl 3,4-dihydroxybenzoate blocked the effect of lysozyme on producing vasodilation in a canine carotid artery preparation. We thought that ethyl gallate showed the most promising response.

Ethyl gallate is added to food as an antioxidant. It is the ethyl ester of gallic acid. Though found naturally in a variety of plant sources including walnuts (8), ethyl gallate is produced from gallic acid and ethanol (9). Moreover, it should be noted that in the above investigations, other potential inhibitors of lysozyme's vasodilatory response, some of which are known to have antioxidant properties, such as gallic acid, propyl gallate, sodium benzoate, limonene, quercetin dihydrate, guaicol, curcumin, ellagic acid, epicathechin gallate from green tea, catechin gallate, epigalloccatechin gallate from green tea, polypheno 60 from green tea, crocin, luteolin, sodium ascorbate, N-acetylcyteine, reduced glutathione, among others, all failed to block lysozyme's vasodilatory effect in the carotid artery preparation. Thus, ethyl gallate, methyl gallate, and ethyl 3,4 dihydroxybenzoate has unique properties for the treatment of septic shock. It is of note that if a substance could not inhibit lysozyme's effect in-vitro, then it would be worthless to pursue an in-vivo study. Even so, the fact that a substance can work in-vitro does not necessarily mean that it will work in-vivo. For instance, mannitol worked in the in-vitro preparation, but did not have a positive effect in-vivo.

SUMMARY OF THE INVENTION

According to a first aspect of the invention, there is provided a method of treating septic shock comprising administering to an individual in need of such treatment an effective amount of ethyl gallate, methyl gallate, or ethyl 3,4 dihydroxybenzoate.

According to a second aspect of the invention, there is provided a method of prophylactically treating septic shock comprising administering to an individual in need of such treatment an effective amount of ethyl gallate, methyl gallate, or ethyl 3,4 dihydroxybenzoate.

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

As discussed herein, we have discovered that ethyl gallate, methyl gallate, and ethyl 3,4 dihydroxybenzoate have unique properties for the treatment of septic shock, for example, in vivo.

According to one aspect of the invention, there is provided a method of treating septic shock comprising administering to an individual in need of such treatment, for example, an individual suffering from sepsis, an effective amount of ethyl gallate, methyl gallate, or ethyl 3,4 dihydroxybenzoate. It is of note that an effective amount is an amount of ethyl-gallate, methyl gallate, or ethyl 3,4 dihydroxybenzoate that is sufficient to lessen the severity of one or more symptoms associated with septic shock, for example but by no means limited to inhibiting or lessening the severity of lysozyme-induced vasodilation and myocardial dysfunction; restoring vasomotor tone; and reversing the reduction in mean arterial pressure.

According to another aspect of the invention, there is provided a method of prophylactically treating septic shock comprising administering to an individual in need of such treatment an effective amount of ethyl gallate, methyl gallate, or ethyl 3,4 dihydroxybenzoate. As will be appreciated by one of skill in the art, such an individual is a patient who has not as yet developed a fall in blood pressure, but who might be expected to develop shock (i.e. low blood pressure) in future hours. In other words, ethyl gallate could be administered in a patient who is septic but has not yet developed shock.

As discussed herein, we have found that in order to adequately achieve control of blood pressure with ethyl-gallate, we maintained a serum range between $9.7 \times 10^{-7}$ mol/L to $4.3 \times 10^{-6}$ mol/L. Accordingly, in one embodiment of the invention, the effective amount is an amount of ethyl gallate, methyl gallate or ethyl 3,4 dihydroxybenzoate sufficient to produce a serum range between $9.7 \times 10^{-7}$ mol/L to $4.3 \times 10^{-6}$ mol/L in the individual in need of such treatment. However, as will be appreciated by one of skill in the art, it is possible that a lower serum concentration may perform similar effects and accordingly it is to be understood that other suitable ranges of an effective amount can easily be determined by one of skill in the art. It is also important to note that other factors may influence what constitutes an effective amount for a particular patient, for example, the age, weight and general condition of the patient.

Specifically, we knew that lysozyme produced hydrogen peroxide from singlet oxygen (7). Therefore, we concentrated on those compounds that could potentially either scavenge singlet oxygen, therefore preventing lysozyme from producing hydrogen peroxide, or could scavenge hydrogen peroxide once it was already formed by lysozyme. We found that ethyl-gallate can scavenge hydrogen peroxide as denoted by multiple methodologies. Moreover, we also found that ethyl-gallate can inhibit the degradation of catalase to compound I. This effect also contributes to ethyl-gallate's inhibiting effect on lysozyme-induced vasodilation and myocardial dysfunction.

Furthermore, ethyl-gallate and the related compounds appear to have unique properties, as discussed herein. There are other phenolic compounds that can scavenge hydrogen peroxide and can also prevent the formation of compound, for instance gallic acid. However, surprisingly, gallic acid could not block the in-vitro effect of lysozyme. Accordingly, while not wishing to be bound to a particular hypothesis or theory, the inventors believe that the geometry of ethyl-gallate (i.e its ability to go to areas where lysozyme has generated hydrogen peroxide) or the different ionic charges of the individual compounds (ie. gallic acid would be dissociated in the plasma while ethyl-gallate does so to a lesser extent) or simply the ability of ethyl-gallate to better get into cells may account for the difference.

In the present study, we examined whether ethyl gallate infusion could reverse the reduction in mean arterial pressure (MAP) that develops in an in-vivo model of *Escherichia coli* septic shock in dogs. We found that ethyl-gallate prevented the decrease in force caused by lysozyme in the carotid artery preparation. In the in-vivo condition, the correlate of this finding is what happens to blood pressure in the intact dog. Again, as noted above, the fact that a substance works in the in-vitro setting does not mean that it works in-vivo. Significantly, we found that ethyl-gallate can work in-vivo as well as in-vitro.

Previously, we provided evidence that ethyl-gallate prevented the vasodilation caused by lysozyme in canine carotid artery and superior mesenteric arterial preparations. In these preparations, we found that lysozyme caused vasodilation by the generation of hydrogen peroxide, and that after hydrogen peroxide is degraded by catalase to compound I, compound I activated guanylyl cyclase to form cyclic-guanosine 3'-5'-monophosphate (cGMP). cGMP then resulted in vasodilation by activation of a protein-kinase G (PKG) dependent pathway. We further demonstrated that ethyl-gallate could scavenge hydrogen peroxide and that it could prevent the formation of compound I to inhibit lysozyme's effect.

Herein, we have looked at the pathway by which peroxacetic acid (POX) caused vasodilation in our carotid and superior mesenteric arterial preparations. POX is a hydroperoxide (slightly different from the molecule of hydrogen peroxide) that also may be released in septic shock by macrophages and inflammatory cells. In these recent experiments, we importantly found that the pathway of vaodilation caused by POX could also be inhibited by ethyl-gallate (see below). However, the pathway by which POX caused vasodilation is much different than that caused by lysozyme. The significance of this finding is that it shows that ethyl-gallate can block pathways other than that induced by lysozyme. To some extent, therefore, the improvement in hemodynamics previously observed when ethyl-gallate was infused in our in-vivo study could have also been related to ethyl-gallate's inhibition of the POX pathway in addition to ethyl-gallate's inhibitory-effect on lysozyme mediated pathways.

The only similarity found between lysozyme and POX is that POX's mechanism of action is also independent of the endothelium and nitric oxide formation, since we could not prevent POX's vasodilatory effect by removal of the endothelium or by nitric oxide inhibition. In contrast to lysozyme, POX seems to cause vasodilation is by activation of an enzyme in the vascular tissue called prostaglandin H synthase (PHS). PHS has an important mechanism of action, in that after activation by hydroperoxides (such as POX), it can in turn activate the cyclooxygenase pathway leading to vasodilation. Indeed, in our current investigation, we found that the vasodilatory effect of POX could be inhibited by indomethacin, an inhibitor of the cyclooxygenase pathway. Furthermore, again unlike lysozyme, we found that the vasodilatory effect of POX could be inhibited by potassium channel blockers, and that POX induced-vasodilation could be prevented by barium and high concentrations of potassium in the organ bath. Further investigation has also suggested that the particular potassium channels implicated were the combination of small (SKCa) and intermediate (IKCa) conductance calcium activated potassium channels, which could be blocked by the combination of apamin and charybdotoxin.

In terms of these experiments, we think that hydroperoxides that are released from inflammatory cells in sepsis could activate the peroxide component of the PHS pathway. This would then activate the cyclooxgenase pathway, thereby leading to prostaglandin synthesis and subsequently to activation of SKCa and IK to produce vasodilation. Thus, inhibition of this pathway by ethyl-gallate may also lead to an improvement in cardiovascular function in septic shock.

Specifically, when a person develops septic shock, their blood pressure becomes very low and they cannot perfuse their vital organs, such as the heart, kidneys, and brain. It is therefore necessary to increase the blood pressure in septic shock. The experiments described above showed that ethyl-gallate can produce this effect.

As will be apparent to one of skill in the art, there are other compounds that are used to treat the fall in blood pressure in septic shock. These substances are known as vasopressors and include norepinephrine, epinephrine, dopamine, phenyleprine, and vasopressin. These agents act on receptors on the vessel to cause vasoconstriction. These agents are used to compensate for the lack of vasomotor tone in septic shock. On the other hand, ethyl-gallate directly acts on a signaling pathway that directly causes the vasodilation in septic shock. Thus, ethyl-gallate gets to the pathogenesis of septic shock, while vasopressors are used just to counteract the vasodilation that would otherwise occur.

Usually, when one increases the blood pressure in septic shock, there is the potential for stroke-volume and cardiac out to fall, since the heart has to pump against a greater load. Particularly, in septic shock, cardiac function is depressed. With ethyl-gallate, we did not find the heart became as depressed, indicating that ethyl-gallate protected the heart from myocardial depression. We know that ethyl-gallate prevents lysozyme-induced myocardial depression from previous in-vitro experiments and that is why stroke-volume and cardiac output did not fall, even though the mean arterial pressure increased with ethyl-gallate (Mink S N, Jha P, Wang, R, Bose D, Jacobs J, Light R B. Effect of continuous arteriovenous hemofiltration combined with systemic vasopressor therapy on depressed left ventricular contractility and tissue oxygen delivery in canine *Escherichia coli* sepsis. Anesthesiology 83: 178-190, 1995)

Thus, we have discovered a new pathway that leads to the cardiovascular dysfunction found in septic shock. This new pathway involves hydrogen-peroxide signaling and this signaling causes the vasodilation and myocardial depression characteristic of this condition. We have further identified lysozyme as one compound that can initiate this signaling pathway, although there may be other proteins capable of generating hydrogen peroxide in this condition. Importantly, we also found a new treatment for the cardiovascular dysfunction that develops in septic shock. Specifically, ethyl-gallate can inhibit hydrogen-peroxide signaling pathway, and this effect can restore vasomotor tone in our experimental septic shock model. In contrast, vasopressor agents do not act on this signaling pathway, but just act on compensatory receptors and therefore do not reverse the underlying pathogenic process.

We speculate moreover that hydrogen peroxide signaling may be important in other conditions leading to distributive shock, such as the systemic inflammatory reaction that accompanies pancreatitis, burns etc. Hydrogen-signaling may also be important in the hypotension that develops after cardiopulmonary bypass.

The objective of this study was to determine if ethyl-gallate treatment could reverse the vasodilatory effect of lysozyme in an in-vivo model of sepsis. We previously showed that ethyl gallate blocked lysozyme's vasodilatory action in an in-vitro preparation, but whether this effect was relevant to what occurs in-vivo was not clear. As previously discussed, just because some compound blocks an in-vitro event, there is no requirement that it will work in-vivo, for instance the mannitol experiment as previously discussed. It is clear, moreover, that the in-vivo condition is obviously more complex than the in-vitro one. The fact that ethyl-gallate worked in-vivo means that it has potential as a therapy in septic shock. The present results show that ethyl-gallate was able to attenuate the systemic vaodilation that occurs in sepsis, and moreover, that this treatment could restore MAP to the presepsis value. The mechanism of ethyl-gallate's effect on MAP was due to vasoconstriction. This was assessed by the increase in SVR that was maintained over the course of the 5 hr study.

When we designed this study, we were unsure what the effect of ethyl-gallate would be on cardiac performance, since systemic vasoconstriction would enhance left ventricular afterload, leading to a decrease in cardiac output, particularly in sepsis (11). It is of note that the heart in the septic shock patient is weak and cannot pump as well as that found for the normal heart. An increase in blood pressure can further reduce stroke-volume and cardiac output. The fact that we did not find this with ethyl-gallate indicates that this treatment also protected the heart from pumping badly. Thus, as discussed herein, ethyl-gallate prevents the myocardial depressant activity caused by lysozyme-induced signaling. However, we found that SV was comparable and SW somewhat higher than corresponding values found in the septic group in which ethyl-gallate was not administered which again indicates that ethyl-gallate can improve heart function by inhibiting lysozyme-induced signaling in septic shock. Furthermore, in this study, we maintained filling pressure (ie Pwp) constant over the course of the study by administration of intravenous volume, so that changes in preload did not contribute to the results of study. We think therefore that in addition to ethyl-gallate's effect on the systemic vasculature, this treatment could block lysozyme's myocardial depressant effect on the heart.

In the design of this study, moreover, we administered the necessary amount of ethylgallate to return MAP to baseline values in an effort to see whether ethyl-gallate had this capability. It is of note that in the clinical arena, one does not necessarily try to return mean arterial pressure to the patient's baseline values, since this would be an unnecessarily high value. One would try to keep blood pressure in the 65-70 mmHg range in a patient in septic shock. In the present study, we tried to restore blood pressure to approximately the baseline value as proof of principle, just to show that ethyl-gallate can actually perform this effect. Whereas these results clearly support this action of ethyl-gallate, it is recognized that in the clinical setting of septic shock, one would aim for more modest increases in MAP since vasoconstriction could potentially decrease organ blood flow which may have harmful effects on oxygen delivery and utilization (10). Even so, we found that serum creatinine, an index of renal function, decreased in the ethyl gallate treated sepsis group, meaning improved renal function, while it increased in the non-treated sepsis group. While improvement in renal function is not necessary for recovery, it will be appreciated by one of skill in the art that the fact that ethyl-gallate improves renal function gives added value to the treatment. Lactate elevations were also more modestly increased in the ethyl-gallate treated group, although this effect did not reach significance between the two sepsis groups. In the ethyl-gallate treated group, moreover, since less normal saline was administered over the course of the study, hemoglobin remained higher at the end of the study as compared with the non-treated ethyl-gallate sepsis group. Finally, we found that serum CK was also lower in the ethyl-gallate treated sepsis group. This would suggest that blood flow to the skeletal muscles was relatively preserved as compared with the non-treated sepsis group, so that less muscle necrosis occurred in the treated group. Thus, in the present study, there is evidence of improved end-organ function, even though MAP was restored to the high baseline values. We think therefore that even greater evidence of improved organ flow could occur if the target MAP had been a more modest one.

While not wishing to be bound to a particular theory or hypothesis, it is noted that ethyl-gallate could primarily inhibit the generation of $H_2O_2$ by lysozyme (7), or inhibit the signaling pathways that are involved in lysozyme's vasodilatory action (2). We previously showed that lysozyme has the intrinsic capacity to generate $H_2O_2$ (7). This generation appears to involve the mechanism described by Wentworth et al in which proteins can utilize water as a catalyst to generate $H_2O_2$ (12) Once formed by lysozyme, $H_2O_2$ then reacts with intrinsic catalase to form a species of catalase termed Compound I (2) Compound I then acts to generate cyclic-guanosine monophosphate which in turn causes vasodilation. In recent experiments, we indeed found that ethyl-gallate can scavenge $H_2O_2$ by multiple techniques that included Amplex Red assay, electrochemical techniques, and glucosidase/glucose assay, discussed herein. We further showed that by wavescan spectroscopy techniques ethyl-gallate can prevent the conversion of catalase to its derivatives. These as well as other mechanisms may account for the efficacy of ethyl-gallate treatment in septic shock.

The dosage of ethyl-gallate given in this study was purely empirical. Others had given the related compound 3,4 dihydroxybenzoate at 250 mg/kg day in mice to improve their physiological response to hypoxia (13), so that for a 20 kg dog this would amount to approximately 5 grams of ethyl-gallate. It is possible that lower doses of ethyl-gallate could produce an effect similar to that achieved in the present study. Moreover, we also showed that ethyl-gallate could be given as bolus form to improve hemodynamics in sepsis and that its effect lasted for over 75 minutes.

When given to the non-septic animal, the preliminary results so far obtained indicate that ethyl-gallate does not increase MAP or SVR. Thus, ethyl-gallate could be administered to a patient who has signs of infection, prior to the development of septic shock, and in this manner, pretreatment may prevent the development of hemodynamic instability that would ordinarily follow. As discussed above, in some embodiments of the invention, ethyl-gallate is administered prophylactically to a patient who has not as yet developed a fall in blood pressure, but who might be expected to develop shock (ie. low blood pressure) in future hours. As such, ethyl-gallate treatment will prevent the development of hydrogen peroxide signaling, so that hypotension and myocardial dysfunction do not occur in this type of patient. In other words, ethyl gallate could be administered in a patient who is septic but has not yet developed shock. It is of note however that if a patient has a normal blood pressure and normal systemic vascular resistance, then one would not want to raise either one of these parameters (ie hypertension would not be beneficial for any patient).

In previous studies, we found that lysozyme is released by white cells in sepsis and that this release may produce systemic vasodilation and myocardial depression (1-7). The novelty of these pathways by which lysozyme produced hemodyamic changes was not previously described until our studies were performed (2, 7). Recent studies have importantly shown that ethyl gallate blocks the effect of lysozyme-induced vasodilation in in-vitro preparations. The present study Indicates that ethyl gallate may reverse the cardiovascular collapse that occurs in an-vivo model of septic shock, and therefore is a treatment for septic shock in the clinical condition.

Figure 1:
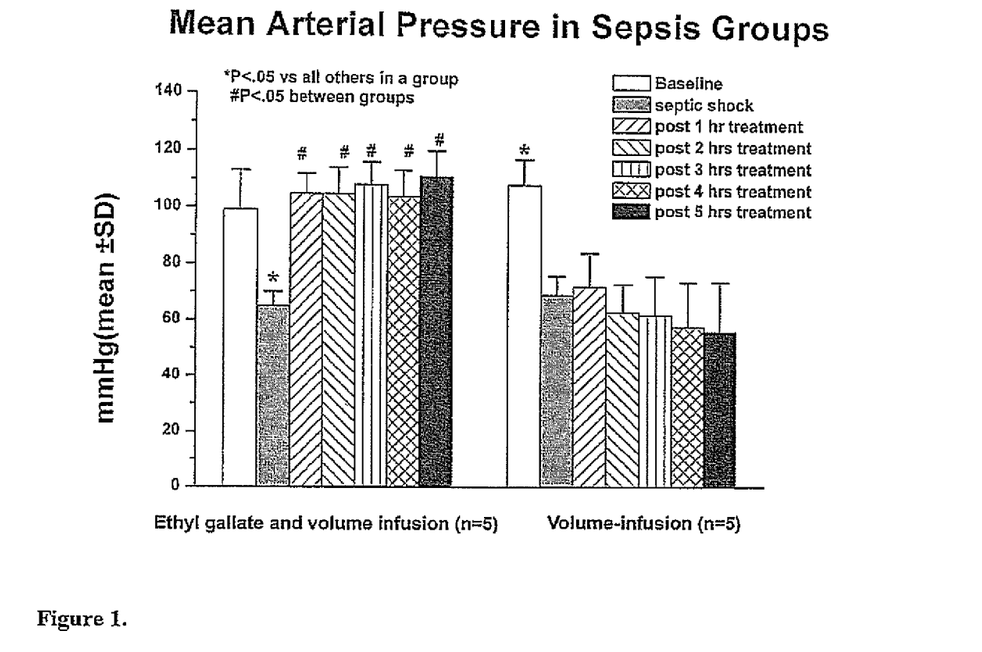
FIG. 1 shows the mean arterial pressure in sepsis groups. Mean arterial pressure fell about 40% from baseline in both groups. Ethyl gallate infusion increased arterial blood pressure to baseline values over the course of the remainder of the study.

FIG. 1 shows the mean arterial pressure in sepsis groups. Mean arterial pressure fell about 40% from baseline in both groups. Ethyl gallate infusion increased arterial blood pressure to baseline values over the course of the remainder of the study.

Figure 2:
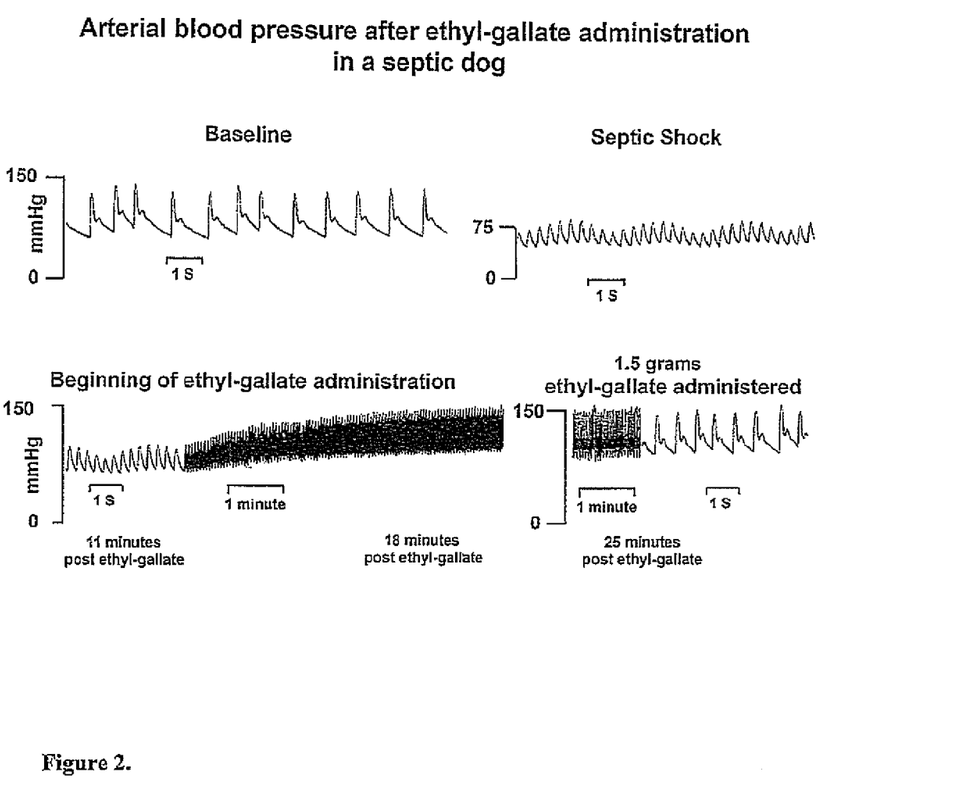
FIG. 2 shows arterial blood pressure after ethyl-gallate administration in a septic dog. In an individual septic dog, after the fall in arterial pressure observed in the septic shock condition, ethyl-gallate infusion increased arterial pressure in approximately 18 minutes where it remained for the duration of the study.

FIG. 2 shows arterial blood pressure after ethyl-gallate administration in a septic dog. In an individual septic dog, after the fall in arterial pressure observed in the septic shock condition, ethyl-gallate infusion increased arterial pressure in approximately 18 minutes where it remained for the duration of the study.

Figure 3:
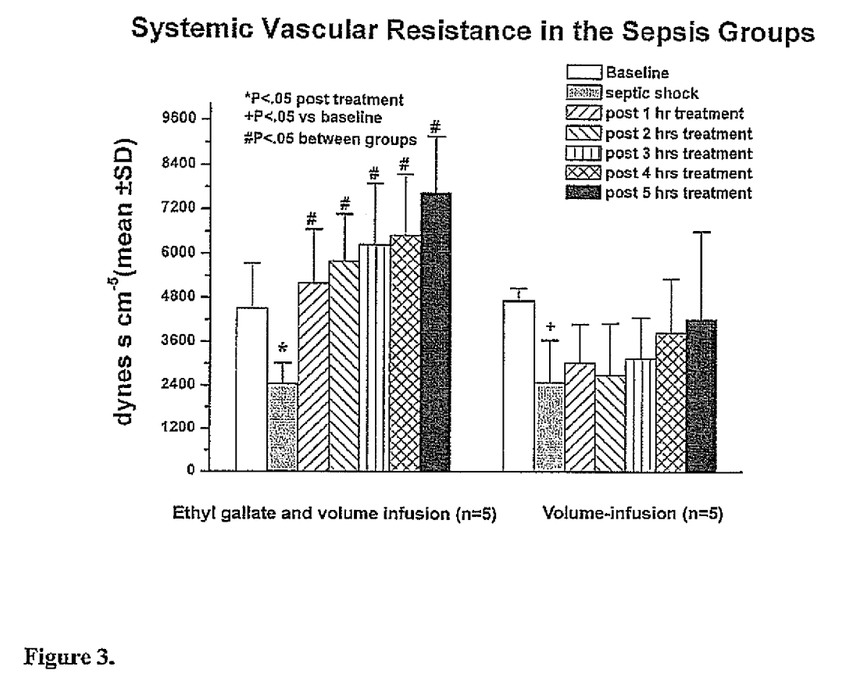
FIG. 3 shows systemic vascular resistance in the sepsis groups. Ethyl-gallate infusion caused an increase in systemic vascular resistance as compared with the septic shock condition that remained for the duration of the study.

FIG. 3 shows systemic vascular resistance in the sepsis groups. Ethyl-gallate infusion caused an increase in systemic vascular resistance as compared with the septic shock condition that remained for the duration of the study.

Figure 4:
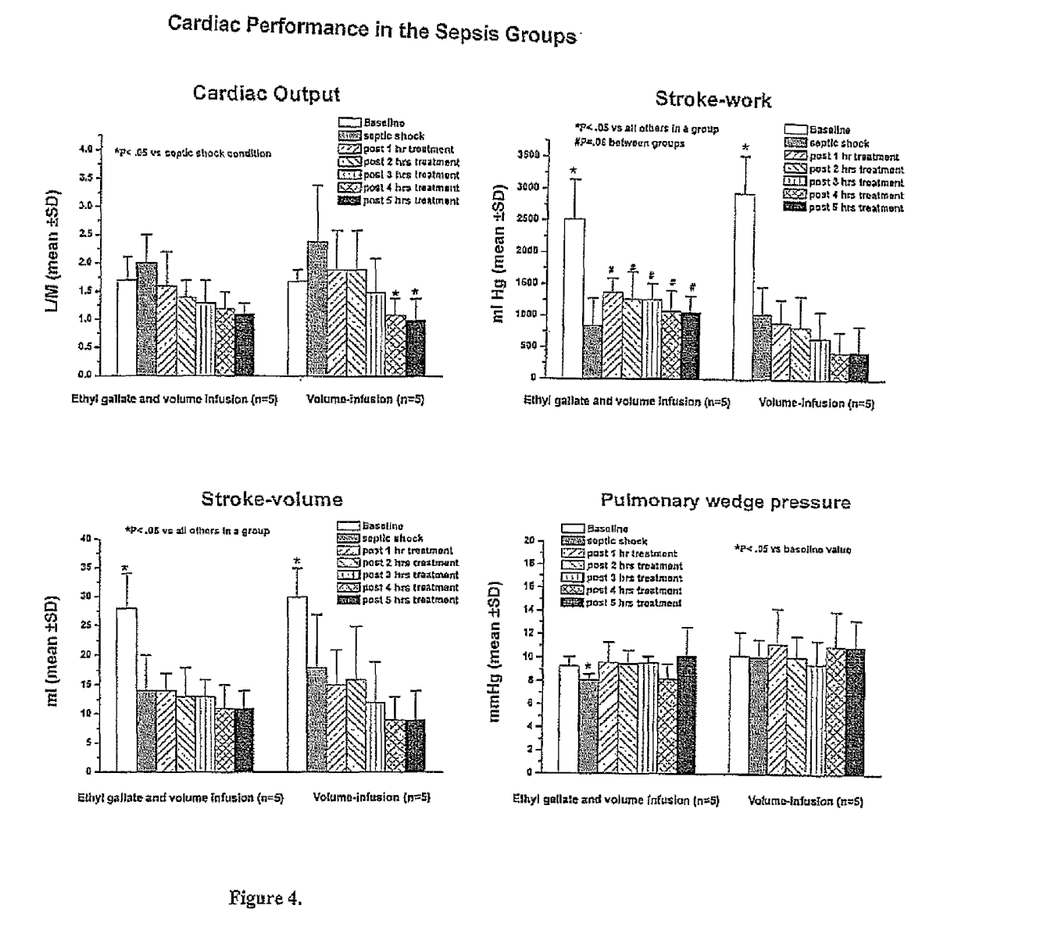
FIG. 4 shows cardiac performance in the sepsis groups. Despite the increase in systemic vascular resistance mediated by ethyl-gallate infusion, cardiac output and stroke volume did not fall as compared with the non-treated group. For similar pulmonary wedge pressures between groups, stroke work appeared higher in the ethyl-gallate treated group.

FIG. 4 shows cardiac performance in the sepsis groups. Despite the increase in systemic vascular resistance mediated by ethyl-gallate infusion, cardiac output and stroke volume did not fall as compared with the non-treated group. For similar pulmonary wedge pressures between groups, stroke work appeared higher in the ethyl-gallate treated group.

Figure 5:
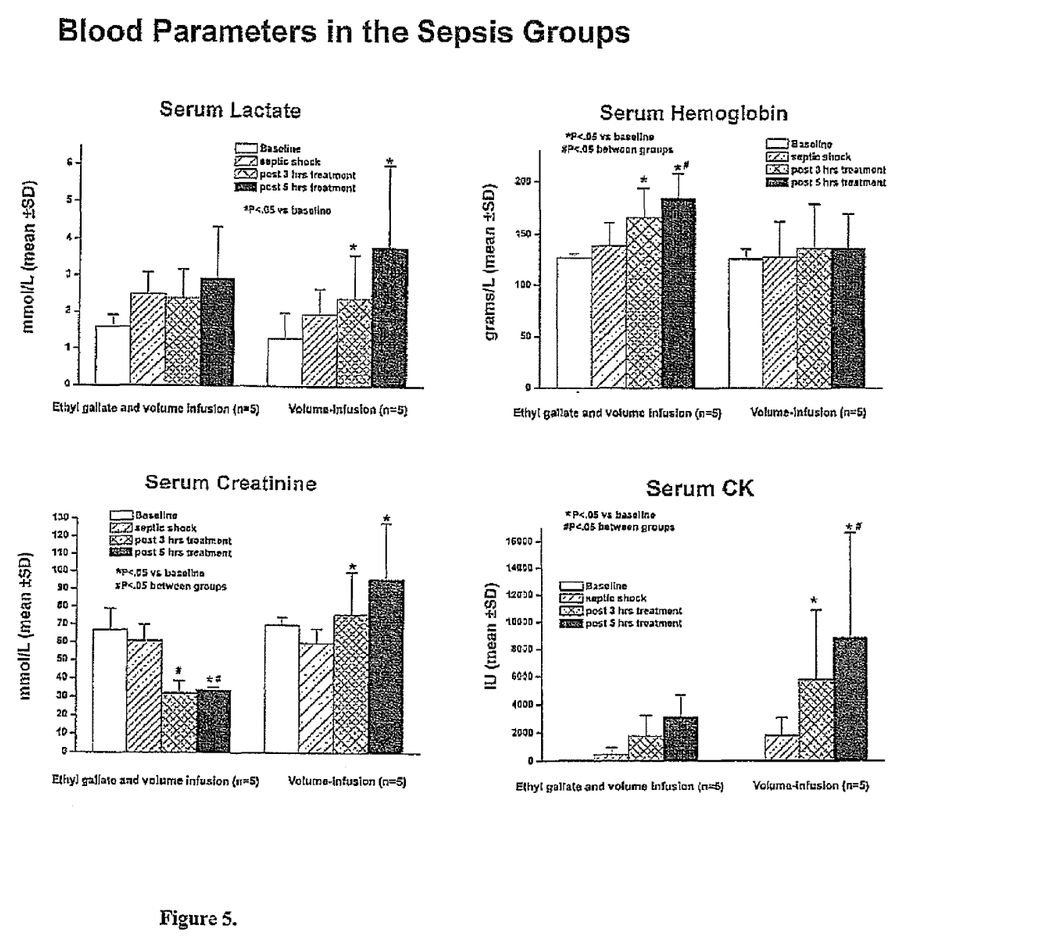
FIG. 5 shows blood parameters in the sepsis groups. In the ethyl-gallate treated group, the increases in lactate were more modest as compared with the non-treated group. In the ethyl-gallate treated group, as assessed by serum creatinine, renal function was improved. In addition, haemoglobin was greater, and evidence of rhadomyolysis (i.e. CK) was less as compared with the non-treated group.

FIG. 5 shows blood parameters in the sepsis groups. In the ethyl-gallate treated group, the increases in lactate were more modest as compared with the non-treated group. In the ethyl-gallate treated group, as assessed by serum creatinine, renal function was improved. In addition, haemoglobin was greater, and evidence of rhadomyolysis (i.e. CK) was less as compared with the non-treated group.

Figure 6:
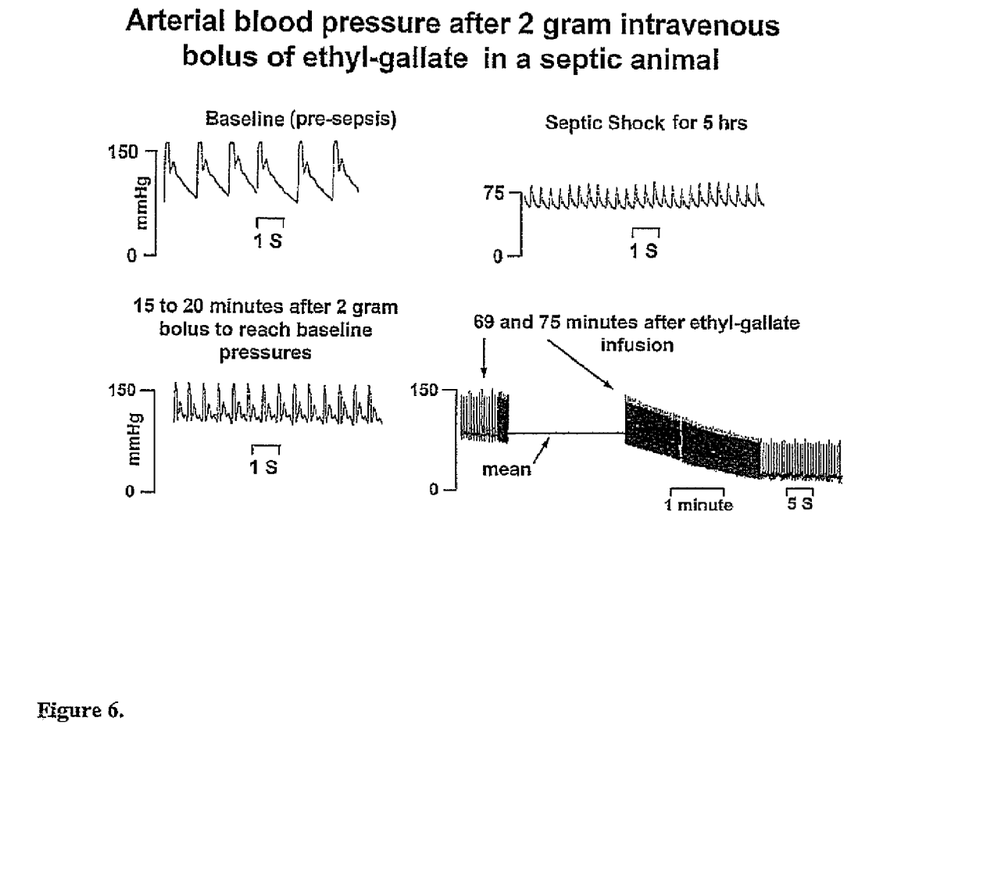
FIG. 6 shows arterial blood pressure after 2 gram intravenous bolus of ethyl gallate in a septic animal. When bolus ethyl-gallate was administered after 5 hours of septic shock, it produced an increase in mean arterial pressure that lasted for over 75 minutes.

FIG. 6 shows arterial blood pressure after 2 gram intravenous bolus of ethyl gallate in a septic animal. When bolus ethyl-gallate was administered after 5 hours of septic shock, it produced an increase in mean arterial pressure that lasted for over 75 minutes.

Figure 7:
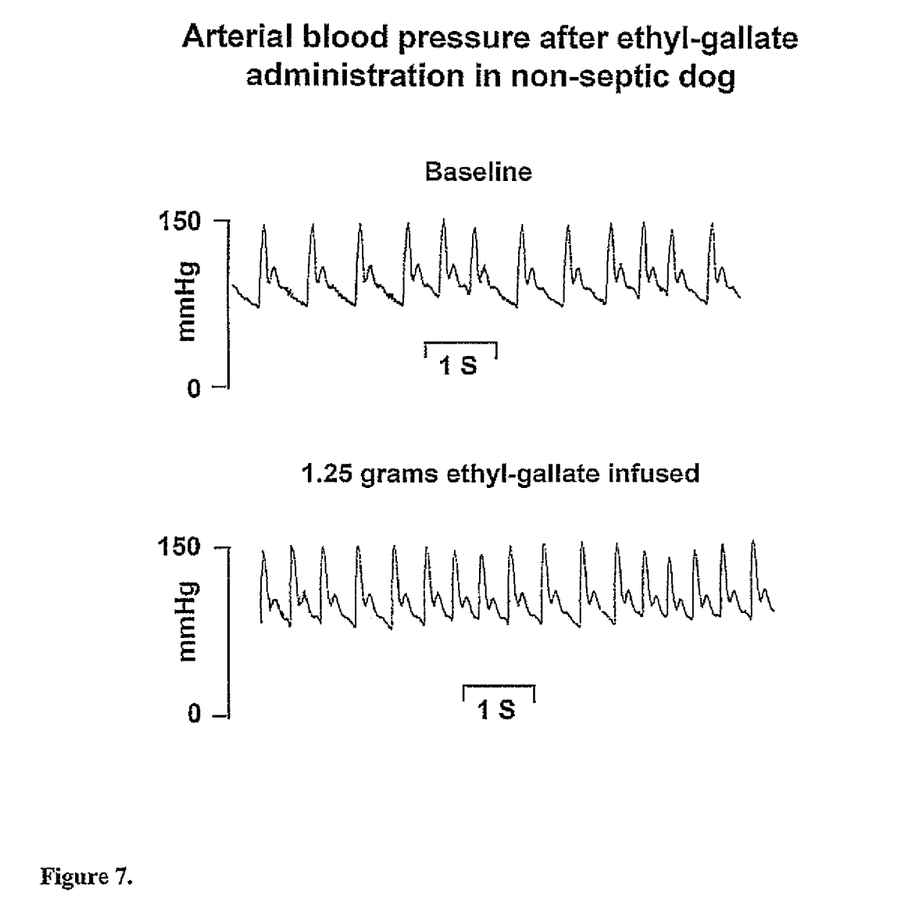
FIG. 7 shows arterial blood pressure after ethyl-gallate administration in non-septic dog. In the non-septic dog, there was a slight tachycardia after ethyl-gallate infusion, but little change in arterial blood pressure.

FIG. 7 shows arterial blood pressure after ethyl-gallate administration in non-septic dog. In the non-septic dog, there was a slight tachycardia after ethyl-gallate infusion, but little change in arterial blood pressure.

Figure 8:
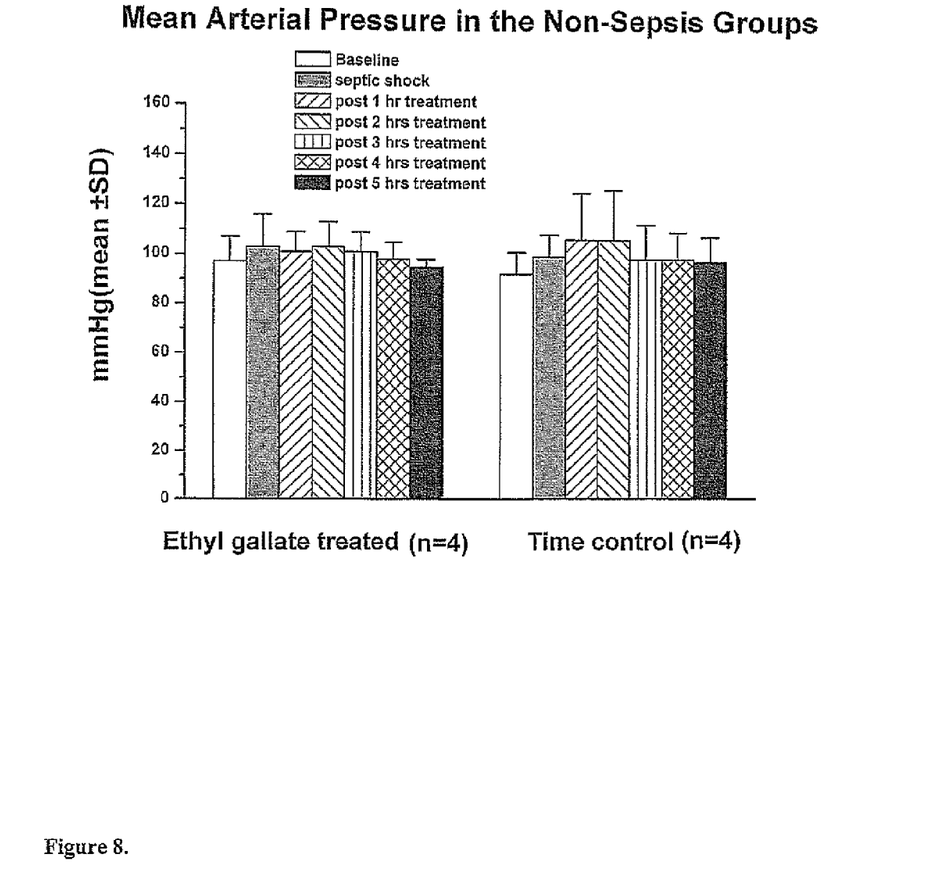
FIG. 8 shows mean arterial pressure in the non-sepsis groups. In the non-septic group, there was no increase in mean arterial pressure after ethyl-gallate infusion.

FIG. 8 shows mean arterial pressure in the non-sepsis groups. In the non-septic group, there was no increase in mean arterial pressure after ethyl-gallate infusion.

Figure 9:
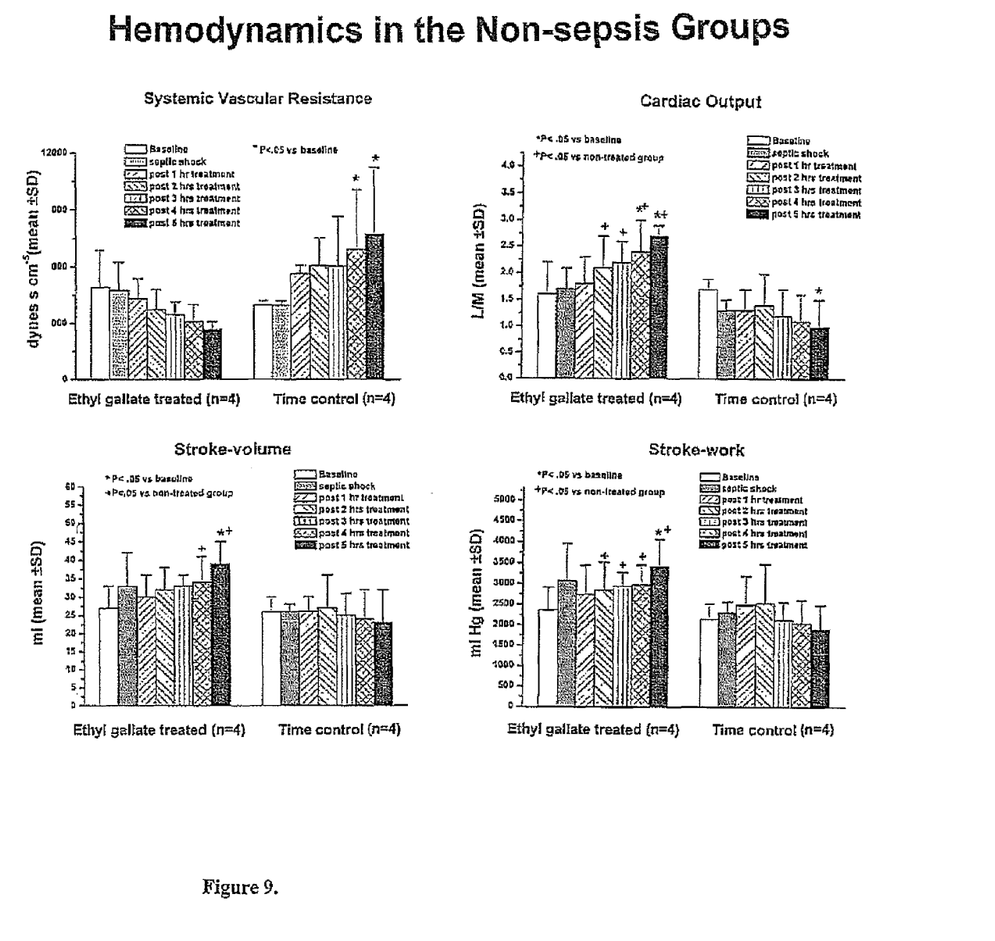
FIG. 9 shows hemodynamics in the non-sepsis groups. In the non-sepsis group, ethyl-gallate did not increase systemic vascular resistance, while stroke-volume cardiac output and stroke-work appeared to increase over the course of the study.

FIG. 9 shows hemodynamics in the non-sepsis groups. In the non-sepsis group, ethyl-gallate did not increase systemic vascular resistance, while stroke-volume cardiac output and stroke-work appeared to increase over the course of the study.

Figure 10:
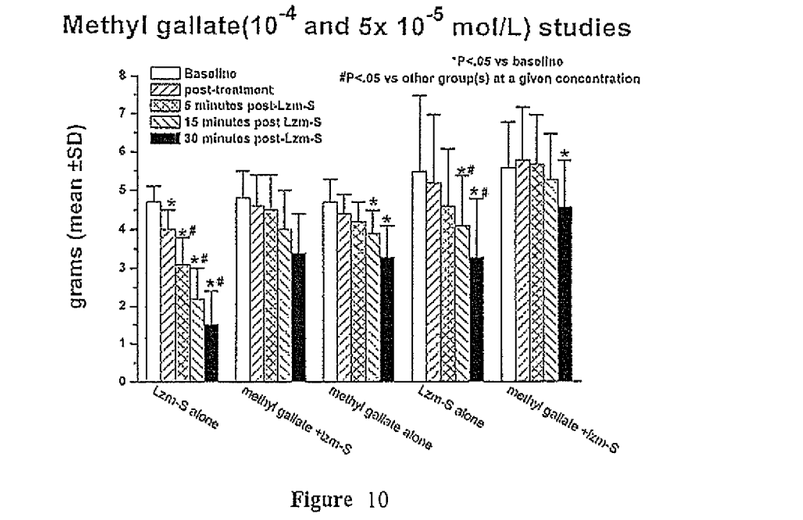
FIG. 10 shows the results of the methyl gallate ($10^{-4}$ and $5 \times 10^{-5}$ mol/L) studies.

FIG. 10 shows the results of the methyl gallate ($10^{-4}$ and $5 \times 10^{-5}$ mol/L) studies.

Figure 11:
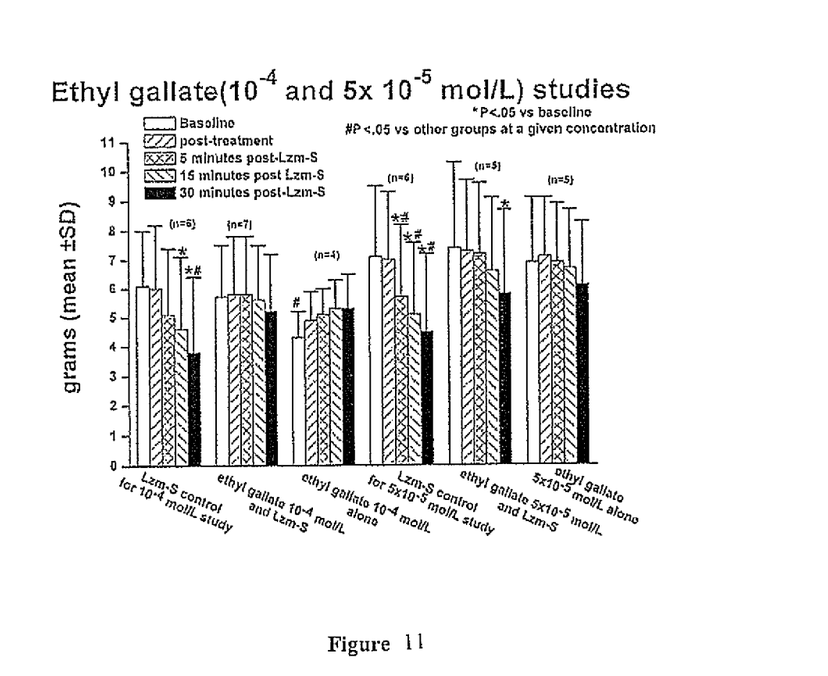
FIG. 11 shows the results of the ethyl gallate ($10^{-4}$ and $5 \times 10^{-5}$ mol/L) studies.

FIG. 11 shows the results of the ethyl gallate ($10^{-4}$ and $5 \times 10^{-5}$ mol/L) studies.

Figure 12:
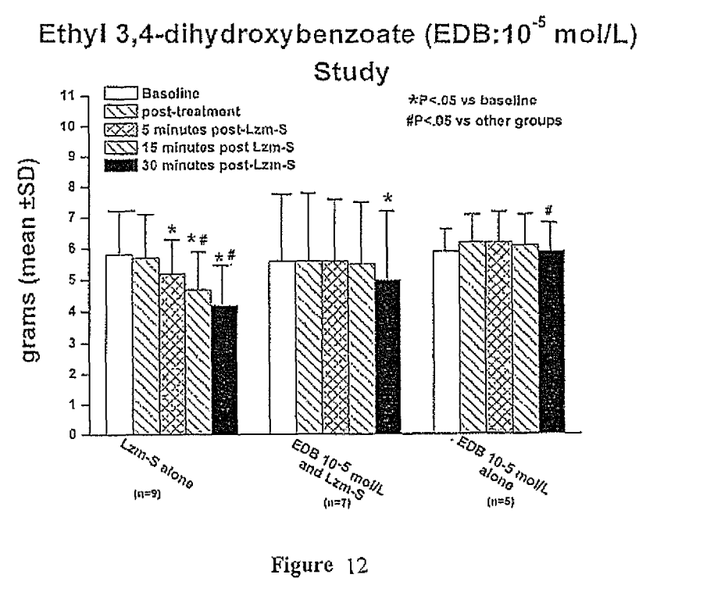
FIG. 12 shows the results of the ethyl 3,4-dihydroxybenzoate (EDB: $10^{-5}$ mol/L) study.
Figure 13:
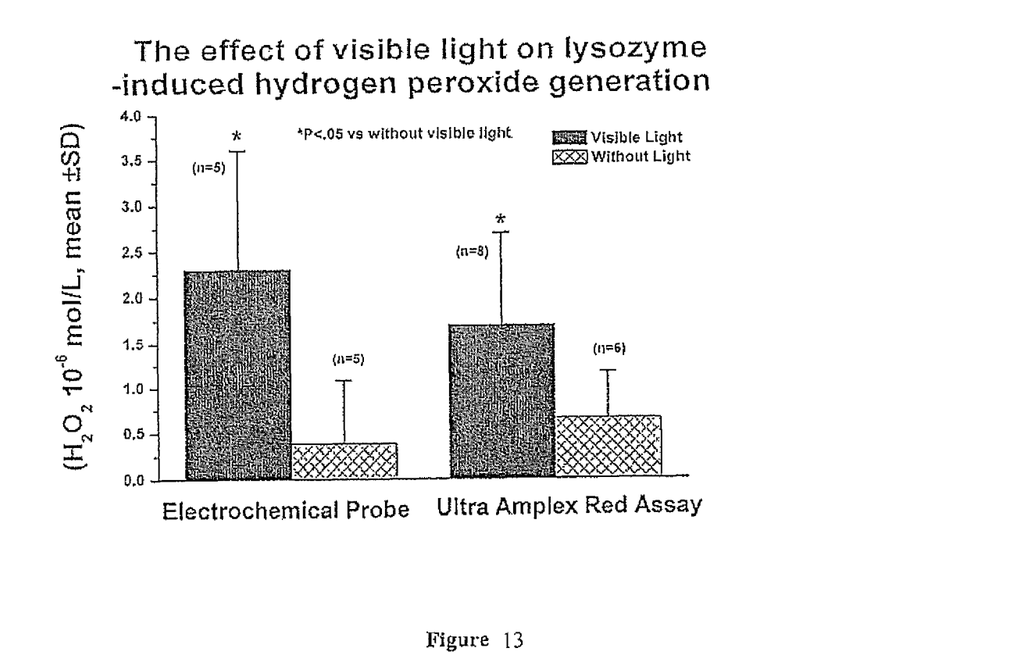
FIG. 13 shows the effect of visible light on lysozyme-induced hydrogen peroxide generation.

FIG. 12 shows the results of the ethyl 3,4-dihydroxybenzoate (EDB: $10^{-5}$ mol/L) study. As discussed herein, FIGS. 11, 12 and 13 show that these three compounds were able to block the effect of lysozyme on vasodilation in the phenylephrine carotid artery preparation. Accordingly, these compounds can be used as a treatment for hemodynamic shock in septic shock or as a prophylactic treatment to prevent septic shock in an individual suffering from sepsis who has not yet progressed to septic shock as discussed herein.

FIG. 13 shows the effect of visible light on lysozyme-induced hydrogen peroxide generation. Specifically, this figure demonstrates that there is little hydrogen peroxide produced when experiments are performed in the dark. It is believed that light activates singlet oxygen which in the presence of lysozyme is able to produce hydrogen peroxide. These results support the notion that singlet oxygen is needed, since lysozyme's effect is attenuated when experiments are performed in the dark.

Figure 14:
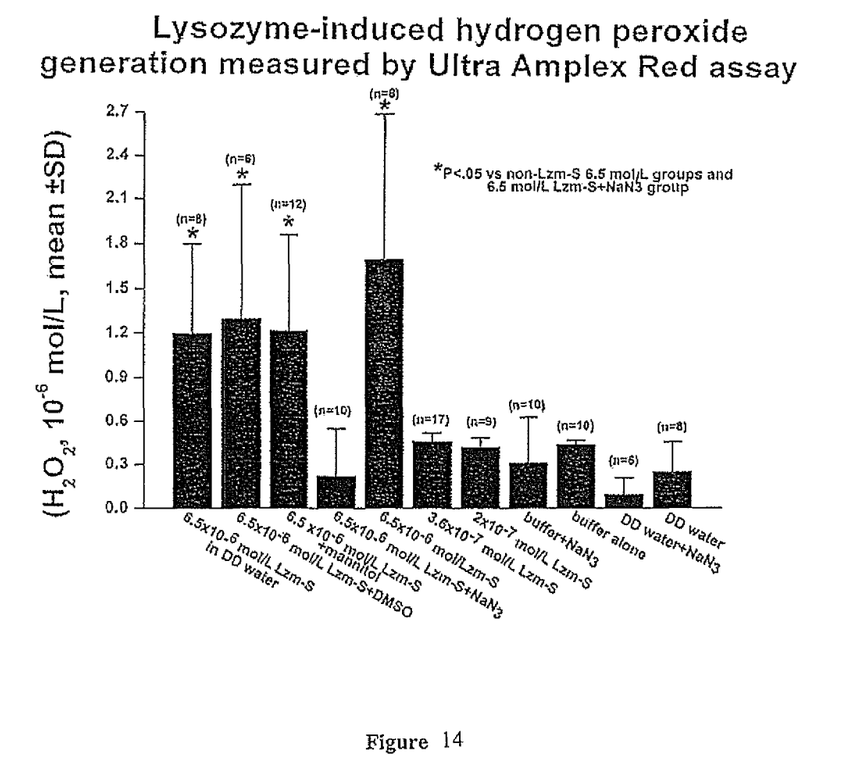
FIG. 14 shows lysozyme-induced hydrogen peroxide generation measured by Ultra Amplex Red assay.

FIG. 14 shows lysozyme-induced hydrogen peroxide generation measured by Ultra Amplex Red assay. In this figure, the results support the view that lysozyme is able to produce hydrogen peroxide at the highest concentration used, i.e $6.5 \times 10^{-6}$ mol/L lysozyme. Moreover, this generation of hydrogen peroxide by lysozyme can be eliminated by the singlet oxygen scavenger, sodium azide (NaN$_3$). Other hydroxyl radical scavengers, such as mannitol and DMSO do not inhibit lysozyme-induced hydrogen peroxide generation.

Results

Septic Groups

In the two sepsis groups, baseline hemodynamic variables (see below) were not different between the ethyl gallate treated and non-ethyl gallate treated groups. None of the dogs died over the course of the study. In the ethyl-gallate treated group, the average time of initiation of treatment after *E coli* infusion was 251±140, while in the placebo treated group, the average time of initiation a comparable amount of placebo (ie. normal saline solution) was 313±68 minutes post baseline. In the two animals in which blood cultures were obtained in the ethyl gallate treated group, *E coli* was grown from the respective blood culture broths.

In the ethyl-gallate treated and non-ethyl-gallate treated groups, MAP at the initiation of either treatment or placebo was not different between groups and had decreased approximately 40% from the baseline value (see FIG. 1). Ethyl gallate infusion caused an increase in MAP that was evident by 20 minutes post infusion (see FIG. 2). Moreover, by 1 hour post-treatment, MAP had returned to the baseline value where it remained over the course of study (see FIGS. 1, 2). The average dose given over the 5 hr period was 4.1±1 grams with a range between 2.6 to 5 grams. In the placebo treated group, MAP remained low over the course of the study.

In the ethyl-gallate treated group, the effect of ethyl-gallate on MAP was to cause an increase in SVR. SVR was significantly increased, both compared with that found in the septic shock condition, and compared with the values found in the non-treated ethyl-gallate septic group. Despite the increase in SVR caused by ethyl-gallate, that in turn would be expected to increase left ventricular afterload (11), CO and SV did not fall in the ethyl-gallate treated group. Indeed, SW was generally higher in the ethyl-gallate treated group over the 5 post-treatment measurement intervals, while Pwp remained unchanged between the two groups (see FIG. 4).

There were only slight changes in Ppa, Rap, and HR over the course of the study that were not different between the two groups (see Table 1). Furthermore, over the period of sepsis, the ventilatory rate was increased in order to reverse the non-ion and ion-gap metabolic acidosis that develops in this model. In both groups, pH and arterial PCO2 fell to similar extents from baseline at the different measurement intervals (see Table 1). Arterial lactate was significantly increased as compared with baseline in the non-treated ethyl-gallate septic group, but the results were not different between the two groups (see FIG. 5 upper left hand panel).

According to the overall design of this study, intravenous volume was administered in both groups to maintain Pwp at the baseline value throughout the study. Significantly less normal saline was required in the ethyl-gallate treated group to achieve this goal (3.38±0.8 L vs 4.7±0.8 L, P<0.05). At the end of the study, serum haemoglobin concentration in the ethylgallate treated group was higher as compared with the non-ethyl gallate treated group (see FIG. 5 right upper hand panel). In addition, in the ethyl-gallate treated group, serum creatinine, the primary index of renal function, decreased over the course of the study which indicated improved renal function, while it increased in the non-ethyl gallate treated group (see FIG. 5 left lower hand panel). There was no difference in urine output between the two groups (see Table 1). Due to rhabdomyolysis, the enzyme creatine kinase increases in this model. This effect appeared greater in the non-treated group (see FIG. 5 right lower hand panel). The remainder of the serum chemistries and haematological parameters are shown in Tables 2A and 2B and were not significantly different between groups.

Of note, moreover, in one animal in the placebo treated group, ethyl-gallate was administered as a bolus after the study was completed to determine whether this approach would also improve hemodynamics in this model (see FIG. 6). The results show that when given by bolus technique, ethyl-gallate caused an increase in MAP in this model that lasts for over 1 hr. Non-septic Groups The effect of ethyl-gallate treatment on hemodynamics in the non-septic animal was different from that found in the septic animal. In this protocol, 5 grams of ethyl-gallate were given in a similar manner over the course of the 5 hr treatment-phase of the study. In contrast to the septic animal, ethyl-gallate treatment did not cause a change in MAP over this period. An example is shown in FIG. 7, while the mean data (n=3) are shown in FIG. 5. In addition, in contrast to the septic group, the results indicate that, if anything, ethyl-gallate treatment caused a decrease in SVR as compared with pre-treatment in the non-septic group (see FIG. 9). Moreover, in this study, CO, SV, and SW all appeared to increase with ethyl-gallate infusion in the non-septic animal (see FIG. 9).

Methods

Overall Design

We have thus far studied 5 dogs in septic shock in which ethyl gallate was infused. We have compared the results obtained in this group with those found in septic animals (n=5) in which this treatment was not given. In addition, in preliminary experiments, we have looked at the effect of ethyl gallate infusion on hemodynamics in non-septic animals (n=3). In a time control non-septic group in which placebo (normal saline solution) was given, we have studied one animal. The results clearly show that ethyl gallate infusion can attenuate the reduction in MAP and systemic vascular resistance (SVR) that occurs in this septic shock model.

E-coli Model and Animal Preparation

The *E coli* model used in the studies was identical to that previously described (2). Sepsis was induced by the intravenous infusion of $10^{10}$ colony forming units of live *E coli* (designation 011:B4). The bacteria were suspended in normal saline solution and were given over 0.5 hour. A constant infusion of approximately $5\times10^9$ colony forming units/hour of *E coli* was then maintained over the duration of the two studies.

The animals (16-24 kg) were initially anesthetized with thiopental sodium (20 mg/kg, intravenously) and constantly infused with sufentanil citrate (1-3 µg/min) and midazolam (5 µg/kg/min) (2). Drug rates were adjusted as required to abolish the palpebral reflex. The animals were placed in the supine position; the trachea was incubated with an endotracheal tube; and the lungs were mechanically ventilated at a tidal volume of 20 ml/kg. The ventilator rate was initially set to maintain blood pH at approximately 7.35. The rate was increased as necessary to reverse the metabolic acidosis that developed over the course of the study. Approximately 100% oxygen was inspired, so that hypoxemia would not affect the results of the study.

Under sterile conditions and by percutaneous techniques (Arrow International, Reading, Pa.) (2), a thermister tipped catheter was advanced from the right jugular vein into the pulmonary artery to measure mean pulmonary arterial pressure (Ppa), mean pulmonary capillary wedge pressure (Pwp), mean right atrial pressure (Rap), and thermodilution cardiac output (CO) (Edwards Lifesciences, Irvine, Calif.). Another introducer was placed into the left jugular vein for administration of intravenous saline solution, the *E coli* infusion, and the treatment or placebo drugs. A catheter was placed into the bladder through the urethra to measure urine output over the course of the study. A polyethylene catheter was percutaneously placed into the femoral artery to measure MAP and to obtain samples of blood for arterial $PO_2$, $PCO_2$, pH, hematocrit (Hct), serum electrolytes and creatinine, liver function tests, and lactate concentrations. The laboratory tests were performed by the clinical laboratories at the Health Sciences Centre.

All vascular catheters were connected to transducers (Cobe, Argon Medical Devices Inc, Athens, Tex.), were referenced relative to the left atrium, and were connected to a chart recorder (Astro-Med, W Warwick, R.I.) (2). Heart rate (HR) was measured from the recorder tracing. Stroke-volume (SV) was calculated as CO/HR. Systemic vascular resistance (SVR) was calculated from [(MAP−Pra)/CO]*80.

Stroke work (SW) was our primary index of cardiac performance and the primary hemodynamic endpoint chosen (2). At constant preload, SW reflects both the decrease in afterload and the change in contractile function that accompany sepsis. SW was determined at approximately the same Pwp at each measurement interval. The baseline Pwp usually averaged ≈8-10 mmHg, and normal saline solution was given as necessary to maintain Pwp constant over the experimental period. SW was calculated from SV*(MAP−Pwp).

Experimental Protocol

The purpose of this study was to determine whether ethyl-gallate could reverse the fall in MAP that occurs in this sepsis model. Ethyl gallate was infused after MAP pressure fell approximately 30 to 40% from the baseline value in which this decline in MAP was not responsive to volume infusion to return Pwp to the baseline value (septic shock condition). This approach would be consistent with that observed in the clinical situation in which vasopressors, such as norepinephrine would be given at this interval. In the two sepsis groups, the animals were allocated in randomized fashion in which one received ethyl-gallate and volume infusion, while in the other, volume infusion alone was given. In the two non-sepsis groups, one received ethyl-gallate while the other received placebo treatment. In the non-sepsis groups, only maintenance volume for anesthesia and for placebo drugs was given over the course of the experiment.

When ethyl gallate was infused, two grams of this substance was dissolved in 250 ml of normal saline solution. A total of approximately 5 grams was administered over the 5 hr period of the study in which 1.5 grams was usually administered over the first hour. The infusion was then titrated to keep MAP at the baseline value. Measurements of hemodynamics were obtained at baseline, once septic shock had been obtained, and at 1 hr, 2 hrs, 3 hrs, 4 hrs, and 5 hrs posttreatment. Before measurements were obtained, Pwp was restored to the baseline value by infusion of normal saline solution. In addition, blood chemistries and arterial blood gas measurements were obtained at baseline, septic shock, and 3 hrs and 5 hrs posttreatment. The animals were sacrificed after completion of the studies.

While the preferred embodiments of the invention have been described above, it will be recognized and understood that various modifications may be made therein, and the appended claims are intended to cover all such modifications which may fall within the spirit and scope of the invention.

REFERENCES

1. Mink S N et al., 2007, Am J Physiol Heart Circ Physiol 293: H3140-3149.
2. Mink S N et al., 2008, Shock 29: 681-687.
3. Mink S N et al., 2008, Am J Physiol Heart Circ Physiol 294: H1724-1735.
4. Mink S N et al., 2005, J Mol Cellular Card 39: 615-625.
5. Mink S N et al., 2003, J Mol Cellular Card 35: 265-275.
6. Mink S N et al., 2004, Critical Care Med 32: 184-193.
7. Mink S N, Jacobs J, Cheng Z Q, Kasian K, Santos-Martinez L E, Light R B. Lysozyme, a new class mediator of sepsis that spontaneously induces generation of hydrogen peroxide to cause cardiovascular dysfunction. In revision, Am J Physiol Heart Circ Physiol.
8. Zhanga et al., 2009, Food Chemistry 113: 160-165.
9. European Patent 137601.
10. Beale R J et al., 2004, Crit Care Med 32: S455-465.
11. Mink S, et al., 1995, Anesthesiology 83: 178-190.
12. Wentworth P, et al., 2001, Science 293: 1806-1811.
13. Kasiganesan H, et al., 2007, Acta Physiol 190: 163-169

TABLE 1

Hemodynamics and arterial blood gas parameters in the sepsis groups

| | Baseline | septic shock | 1 hr post | 2 hrs post | 3 hrs post | 4 hrs post | 5 hrs post |
|---|---|---|---|---|---|---|---|
| Ethyl gallate and volume infusion group (n = 5) | | | | | | | |
| HR (beats/min) | 59 ± 8* | 145 ± 33 | 116 ± 47 | 111 ± 33 | 107 ± 34 | 115 ± 36 | 110 ± 34 |
| Ppa (mmHg) | 16 ± 1.3 | 15 ± 2.3 | 18 ± 4.8 | 18 ± 5 | 21 ± 6 | 21 ± 9 | 23 ± 7* |
| Rap (mmHg) | 9 ± 1.2 | 7 ± 1.3 | 8 ± 1.3 | 8.6 ± 1.7 | 8.8 ± 0.8 | 9.2 ± 1.1 | 8.6 ± 1.3 |
| Arterial pH | 7.38 ± .0.02 | 7.26 ± .06* | — | — | 7.21 ± .08* | — | 7.14 ± .06* |
| $PCO_2$ (mmHg) | 29 ± 4 | 27 ± 4 | — | — | 21 ± 2*# | — | 19 ± 2* |
| Urine-volume (ml) | — | 45 ± 34 | 67 ± 58 | 42 ± 19 | 42 ± 19 | 36 ± 26 | 36 ± 26 |
| Volume infusion group (n = 5) | | | | | | | |
| HR (beats/min) | 56 ± 6* | 137 ± 26 | 132 ± 42 | 136 ± 43 | 137 ± 41 | 138 ± 32 | 128 ± 28 |
| Ppa (mmHg) | 18 ± 2.5 | 17 ± 2 | 17 ± 2 | 17 ± 2 | 17 ± 2 | 18 ± 4 | 20 ± 4 |
| Rap (mmHg) | 9.3 ± 1.6 | 7.5 ± 1.7 | 8.2 ± 2.8 | 8.3 ± 2.2 | 8.1 ± 2.2 | 8.3 ± 2.6 | 8.4 ± 2.1 |
| Arterial pH | 7.41 ± .0.03 | 7.29 ± .05* | — | — | 7.19 ± .05*# | — | 7.11 ± ..07*# |

TABLE 1-continued

Hemodynamics and arterial blood gas parameters in the sepsis groups

|  | Baseline | septic shock | 1 hr post | 2 hrs post | 3 hrs post | 4 hrs post | 5 hrs post |
|---|---|---|---|---|---|---|---|
| $PCO_2$ (mmHg) | 31 ± 5 | 26 ± 5 | — | — | 24 ± 5* | — | 22 ± 4* |
| Urine-volume (ml) | — | 51 ± 39 | 85 ± 75 | 75 ± 72 | 45 ± 51 | 15 ± 16 | 15 ± 23 |

Mean (± SD). Measurements were obtained at baseline, septic shock, and 1 hr, 2 hrs, 3 hrs, 4 hrs, and 5 hrs after ethyl gallate and placebo treatment in the respective groups.
HR is heart rate;
Ppa is pulmonary artery pressure;
Rap is right atrial pressure;
PH and $PCO_2$ are arterial pH and arterial partial pressure of carbon-dioxide, respectively.
Urine volume (ml) per hour over the course of sepsis is also shown.
*$P < .05$ vs baseline;
$P < .05$ vs previous condition by two-way analysis of variance and Student Newman-Keuls' multiple comparison test.

TABLE 2A

Blood chemistries and hematology parameters in the ethyl gallate and volume infusion septic group (n = 5)

|  | Baseline | septic shock | 3 hrs post | 5 hrs post |
|---|---|---|---|---|
| sodium (mmol/L) | 151 ± 2 | 150 ± 7+ | 152 ± 5 | 153 ± 6 |
| total $CO_2$ (mmol/L) | 21 ± 3 | 18 ± 2* | 14 ± 2* | 14 ± 2* |
| chloride (mmol/L) | 118 ± 3 | 123 ± 8*+ | 130 ± 6* | 130 ± 7* |
| AST (IU) | 18 ± 4 | 137 ± 130 | 268 ± 162 | 337 ± 141 |
| ALT (IU) | 52 ± 20 | 139 ± 116 | 210 ± 90 | 236 ± 56 |
| LD (IU) | 26 ± 4 | 128 ± 82 | 253 ± 172* | 335 ± 175* |
| bilirubin (mmol/L) | 3.4 ± 1 | 9.2 ± 3.6* | 11 ± 4.5* | 12.4 ± 4* |
| Alk P'tase | 31 ± 11 | 41 ± 27 | 54 ± 36 | 91 ± 39* |
| glucose (mmol/L) | 5.5 ± 0.3 | 5.3 ± 0.3 | 4.4 ± 1.5 | 3.6 ± 2.2 |
| WBC ×$10^9$/L | 3.2 ± 1.9 | 1.3 ± 0.7 | 2.1 ± 1.9 | 2.64 ± 2.3 |
| Platelets ×$10^9$/L | 196 ± 18 | 117 ± 27* | 100 ± 37* | 74 ± 21* |

Mean (±SD). Measurements were obtained at baseline, after septic shock, and after 3 hrs and 5 hrs post ethyl-gallate treatment, ALT, AST, LD, Alk P'tase (in international units), and WBC are alanine transaminase, aspartate transaminase, lactate dehydrogenase, alkaline phosphatase, and white blood cell count respectively.
*$P < .05$ vs baseline,
$P < .05$ between groups two-way analysis of variance and Student Newman- Keuls' multiple comparis

TABLE 2B

Blood chemistries and hematology parameters in the volume infusion septic group (n = 5)

|  | Baseline | septic shock | 1 hr post | 2 hrs post |
|---|---|---|---|---|
| sodium (mmol/L) | 154 ± 3 | 156 ± 2 | 157 ± 3 | 157 ± 3 |
| total $CO_2$ (mmol/L) | 24 ± 3 | 18 ± 2* | 16 ± 2* | 14 ± 1* |
| chloride (mmol/L) | 118 ± 2 | 130 ± 4* | 134 ± 6* | 135 ± 6* |
| AST (IU) | 16 ± 7 | 309 ± 287 | 534 ± 537* | 717 ± 692* |
| ALT (IU) | 115 ± 131 | 396 ± 407 | 521 ± 612 | 568 ± 679 |
| LD (IU) | 39 ± 11 | 183 ± 104 | 347 ± 227* | 487 ± 280* |
| bilirubin (mmol/L) | 3 ± 1.2 | 8.8 ± 5.2* | 9.6 ± 5.6* | 10.2 ± 3.5* |
| Alk P'tase | 35 ± 15 | 41 ± 26 | 63 ± 38 | 87 ± 57* |
| glucose (mmol/L) | 5.6 ± 0.4 | 5.0 ± 0.3 | 3.7 ± 1.3 | 3.1 ± 2.6 |
| WBC ×$10^9$/L | 4.3 ± 2.4 | 1.9 ± 1.3 | 3.1 ± 2.5 | 3.3 ± 2.4 |
| Platelets ×$10^9$/L | 205 ± 53 | 95 ± 50* | 55 ± 19* | 48 ± 10* |

Mean (±SD). Measurements were obtained at baseline, after septic shock, and after 3 hrs and 5 hrs post placebo treatment. ALT, AST, LD, Alk P'tase (in international units), and WBC are anine transaminase, aspartate transaminase, lactate dehydrogenase, alkaline phosphatase, and white blood cell count respectively.
*$P < .05$ vs baseline,
$P < .05$ between groups two-way analysis of variance and Student Newman- Keuls' multiple comparison test.

The invention claimed is:

1. A method of treating septic shock comprising administering to an individual in need of such treatment an effective amount of ethyl gallate, methyl gallate, or ethyl 3,4 dihydroxybenzoate.

2. The method according to claim 1 wherein the effective amount is an amount ethyl gallate, methyl gallate or ethyl 3,4 dihydroxybenzoate sufficient to produce a serum range between $9.7 \times 10^{-7}$ mol/L to $4.3 \times 10^{-6}$ mol/L in the individual in need of such treatment.

3. A method of prophylactically treating septic shock comprising administering to an individual in need of such treatment an effective amount of ethyl gallate, methyl gallate, or ethyl 3,4 dihydroxybenzoate.

4. The method according to claim 3 wherein the effective amount is an amount ethyl gallate, methyl gallate or ethyl 3,4 dihydroxybenzoate sufficient to produce a serum range between $9.7 \times 10^{-7}$ mol/L to $4.3 \times 10^{-6}$ mol/L in the individual in need of such treatment.

* * * * *